(12) United States Patent
Addy

(10) Patent No.: US 10,633,318 B2
(45) Date of Patent: Apr. 28, 2020

(54) WAX ETHERS AND RELATED METHODS

(71) Applicant: International Flora Technologies, Ltd., Chandler, AZ (US)

(72) Inventor: Jeff Addy, Chandler, AZ (US)

(73) Assignee: International Flora Technologies, Ltd., Chandler, AZ (US)

( * ) Notice: Subject to any disclaimer, the term of this patent is extended or adjusted under 35 U.S.C. 154(b) by 0 days.

(21) Appl. No.: 16/364,033

(22) Filed: Mar. 25, 2019

(65) Prior Publication Data

US 2019/0292121 A1 Sep. 26, 2019

Related U.S. Application Data

(60) Provisional application No. 62/648,059, filed on Mar. 26, 2018.

(51) Int. Cl.
*C07C 41/01* (2006.01)
*B01J 27/08* (2006.01)

(52) U.S. Cl.
CPC .............. *C07C 41/01* (2013.01); *B01J 27/08* (2013.01)

(58) Field of Classification Search
CPC .............................. C07C 41/01; B01J 27/125
See application file for complete search history.

(56) References Cited

U.S. PATENT DOCUMENTS 9,873,843 B2    1/2018   Nicolosi et al.

FOREIGN PATENT DOCUMENTS

| DE | 102012210556 A1 | 12/2013 |
| WO | 2013010747 A1 | 1/2013 |
| WO | 2017040720 A1 | 3/2017 |

OTHER PUBLICATIONS

International Search Report, PCT Patent Application No. PCT/US2019/024035, dated Jun. 20, 2019, 2 pages.
Berger, et al., "Carba Analogues of Triglycerides—Isometeric Mimics for Natural Lipids. Novel Substrates for the Determination of Regio- and Enantioselectives Displayed by Lipases," Bioorganic & Medicinal Chemistry, vol. 2, No. 7, 1994, pp. 573-588.
Baumann, et al., "Reactions of Aliphatic Methanesulfonates. I. Syntheses of Long Chain Glyceryl-(1) Ethers," J. Org. Chem., 1964, 29 (10), pp. 3055-3057.
Baumann, et al., "Reactions of Aliphatic Methanesulfonates. II. Syntheses of Long-Chain Di- and Trialkyl Glyceryl Ethers," J. Org. Chem., 1966, 31 (2), pp. 498-500.
Biermann, et al., "Synthesis of Ethers by Ga Br 3-Catalyzed Reduction of Carboxylic Acid Esters and Lactones by Siloxanes," ChemSusChem, 2014, 7: 644-649, doi:10.1002/cssc.201300627.
Choi, et al., "Kinetics and Relative Rates of the Gallium Bromide-Catalyzed Reactions of Alkyl Bromides with Aromatic Hydrocarbons in 1,2,4-Trichlorobenzene Solution," J. Am. Chem. Soc., 1963, 85 (17), pp. 2596-2599.
Go, et al., "Synthesis of Long Chain Alkyl Glyceryl Ethers From Triglycerides Using Boron Trifluoride Etherate and Lithium Aluminum Hydride," J. of the Amer. Oil Chem. Soc., 1975, 52.427-429, 10.1007/BF02545283.
Hansen, et al. "Convenient Two-Step Conversion of Lactones into Cyclic Ethers," J. Org. Chem., 1998, 63 (7), pp. 2360-2361.
Li, et al., "A Gallium-Catalyzed Cycloisomerization/Friedel-Crafts Tandem," J. Org. Chem., 2010, 75 (24), pp. 8435-3449.
Robert, et al., "Si—H Bond Activation: Bridging Lewis Acid Catalysis with Brookhart's Iridium(III) Pincer Complex and B(C6F5)3," Angew. Chem. Int. Ed., 2013, 52: 5216-5218. doi:10.1002/anie.201301205.
Sutter et al., "Selective Synthesis of 1-0-Alkyl(poly)glycerol Ethers by Catalytic Reductive Alkylation of Carboxylic Acids with a Recyclable Catalytic System," ChemSusChem, 2012, 5: 2397-2409, doi:10.1002/cssc.201200447.
Biermann, et al., Cross-metathesis of Unsaturated Triglycerides with Methyl Acrylate: Synthesis of a Dimeric Metathesis Product, Eur. J. Lipid Sci. Technol. 2011, 113, pp. 33-45.

*Primary Examiner* — Rosalynd A Keys
(74) *Attorney, Agent, or Firm* — Adam R. Stephenson, Ltd.

(57) ABSTRACT

Implementations of a method of forming a wax ether composition may include: providing a batch of lipids, drying the batch of lipids, and cooling the batch of lipids. The method may also include dosing, with a catalyst, the batch of lipids at 0.1% to 0.3% by weight of the batch of lipids and dissolving the catalyst in the batch of lipids to form a homogenous solution. The method may include adding at least a molar equivalent of a hydrogen donor to the homogenous solution. The method may include sealing and maintaining the homogenous solution and hydrogen donor under atmospheric pressure under reflux until a chemical reaction between the homogenous solution and the hydrogen donor forms a product comprising an ether.

20 Claims, 3 Drawing Sheets

WAX ETHERS AND RELATED METHODS

CROSS REFERENCE TO RELATED APPLICATIONS

This document claims the benefit of the filing date of U.S. Provisional Patent Application 62/648,059, entitled "Wax Ethers and Related Methods" to Jeff Addy et al. which was filed on Mar. 26, 2018, the disclosure of which is hereby incorporated entirely herein by reference.

BACKGROUND

1. Technical Field

Aspects of this document relate generally to wax ethers, such as methods of forming wax ethers from lipids. More specific implementations involve ether lipids sourced from botanical raw materials.

2. Background

In organic chemistry, an ether is a carbon-containing molecule that includes the ether functional group (—C—O—C—) in part of its molecular structure.

SUMMARY

Implementations of a method of forming an ether composition may include: providing a batch of lipids, drying the batch of lipids, and cooling the batch of lipids. The method may also include dosing, with a catalyst, the batch of lipids at 0.1% to 0.3% by weight of the batch of lipids and dissolving the catalyst in the batch of lipids to form a homogenous solution. The method may include adding at least a molar equivalent of a hydrogen donor to the homogenous solution. The method may include sealing and maintaining the homogenous solution and hydrogen donor under atmospheric pressure under reflux until a chemical reaction between the homogenous solution and the hydrogen donor forms a product comprising an ether.

Implementations of methods of forming ether compositions may include one, all, or any of the following:

Drying the batch of lipids may include heating the batch of lipids at 100 C under agitation and vacuum.

Cooling the batch of lipids may include cooling the batch of lipids to 5 C-10 C above the melting point of the lipids under agitation and vacuum.

The method may further include removing a residue of the hydrogen donor through one of vacuum distillation or physical separation.

The method may further include capturing and redistributing the hydrogen donor using a condenser during the chemical reaction.

The batch of lipids may include wax esters or triglycerides.

The hydrogen donor may include 1,1,3,3-Tetramethyldisiloxane (TMDS).

The catalyst may be a metal halide.

Implementations of a method of forming an ether composition may include: providing a batch of triglycerides, drying the batch of triglycerides, and cooling the batch of triglycerides. The method may also include dosing, with a catalyst, the batch of triglycerides at 0.1% to 0.3% by weight of the batch of triglycerides and dissolving the catalyst in the batch of triglycerides to form a homogenous solution. The method may include adding at least a molar equivalent of a hydrogen donor to the homogenous solution. The method may include sealing and maintaining the homogenous solution and the hydrogen donor under atmospheric pressure under reflux until a chemical reaction between the homogenous solution and the hydrogen donor is complete.

Implementations of methods of forming ether compositions may include one, all, or any of the following:

Drying the batch of lipids may include heating the batch of triglycerides at 100 C under agitation and vacuum.

Cooling the batch of triglycerides may include cooling the batch of triglycerides to 5 C-10 C above the melting point of the batch of triglycerides under agitation and vacuum.

The method may further include removing a residue of the hydrogen donor through one of vacuum distillation or physical separation.

The method may further include capturing and redistributing the hydrogen donor using a condenser during the chemical reaction.

A product of the chemical reaction may include an iodine value of 52 and a melting point of 45 C.

Implementations of a method of forming a wax ether composition may include: providing a batch of wax esters, drying the batch of wax esters, and cooling the batch of wax esters. The method also includes dosing, with a catalyst, the batch of wax esters at 0.1% to 0.3% by weight of the batch of wax esters and dissolving the catalyst in the batch of wax esters to form a homogenous solution. The method includes adding at least a molar equivalent of a hydrogen donor to the homogenous solution. The method includes sealing and maintaining the homogenous solution and the hydrogen donor under atmospheric pressure under reflux until a chemical reaction between the homogenous solution and the hydrogen donor forms a product comprising an ether.

Implementations of methods of forming ether compositions may include one, all, or any of the following:

The batch of wax esters may include wax esters having carbon chain lengths ranging from C24 to C52.

Drying the batch of wax esters may include heating the batch of wax esters at 100 C under agitation and vacuum.

Cooling the batch of wax esters may include cooling the batch of wax esters to 5 C-10 C above the melting point of the batch of wax esters under agitation and vacuum.

The method may further include removing a residue of the hydrogen donor through one of vacuum distillation or physical separation.

The method may further include capturing and redistributing the hydrogen donor using a condenser during the chemical reaction.

The foregoing and other aspects, features, and advantages will be apparent to those artisans of ordinary skill in the art from the DESCRIPTION and DRAWINGS, and from the CLAIMS.

BRIEF DESCRIPTION OF THE DRAWINGS

Implementations will hereinafter be described in conjunction with the appended drawings, where like designations denote like elements, and.

DESCRIPTION

Figure 1:
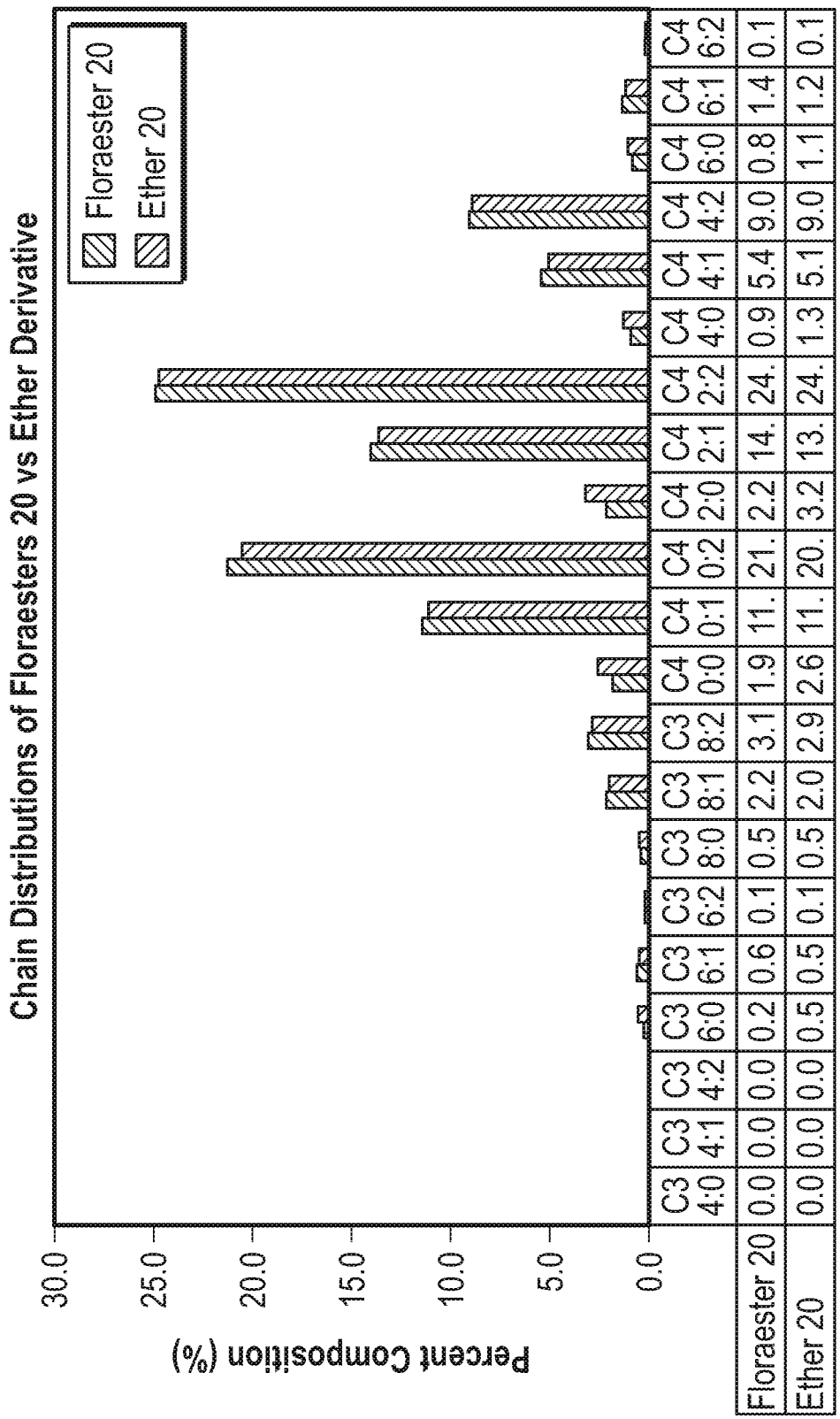
FIG. 1 is a graph illustrating carbon chain length distributions between reactants and products from an implementation of a method of forming wax ethers.

This disclosure, its aspects and implementations, are not limited to the specific components, assembly procedures or method elements disclosed herein. Many additional components, assembly procedures and/or method elements known in the art consistent with the intended methods of forming wax ethers will become apparent for use with particular implementations from this disclosure. Accordingly, for example, although particular implementations are disclosed, such implementations and implementing components may comprise any shape, size, style, type, model, version, measurement, concentration, material, quantity, method element, step, and/or the like as is known in the art for such wax ethers, and implementing components and methods, consistent with the intended operation and methods.

In various implementations, lipids that are classified as wax-esters can be derivatized into different compounds. During a reduction reaction, ester functional groups on the reactant are reduced to ethers. Under specific conditions, points of unsaturation on the ethers may also cleave to form low-boiling point carbon chains with functional groups of alkanes, alkenes, ketones, and aldehydes. In various implementations of methods disclosed in this document, a catalyst is used to carry out the reduction reaction. In various implementations, the method may employ a catalyst such as, by non-limiting example, a metal halide such as, by non-limiting example, gallium bromide (GaBr3) in combination with a hydrogen donor such as, by non-limiting example, 1,1,3,3-tetramethyldisiloxane (TMDS).

Implementations of a method of forming wax ethers from wax esters may employ a batch reaction process. In a particular implementation of the process, the method includes providing a batch of lipids (input material) and drying the batch of lipids at 100 C under constant agitation and full vacuum until substantially all water has evaporated from the material. The batch of lipids are then be cooled to 5 C-10 C above the melting point of the lipid while the batch of lipids is still under agitation and vacuum. Vacuuming of the batch of lipids is then stopped and the catalyst is then dosed at 0.1% to 0.3% by weight of the lipid, depending on the input material. In various implementations of a method of forming wax ethers, triglycerides or other similar material may be used as the input material. After the catalyst has dissolved and the solution is homogenous, a molar equivalent plus about 0-10% excess of TMDS or other hydrogen donor on a molar basis is added to the reactor. A molar equivalent, as used herein, is an amount of a substance that will supply the reaction with one mole of hydrogen protons. In various implementations, however, other hydrogen donor reactants other than TMDS or in combination with TMDS may be added to the reactor.

After addition of the catalyst and the hydrogen donor reactant, the reactor is then sealed and maintained under atmospheric pressure under reflux until the reaction is complete. In various implementations, the time for completion of the reaction may last around 30 minutes. In other implementations, the reaction may take more than 30 minutes or less than 30 minutes depending on the particular reactants involved. During the reaction, a condenser is used to capture and redistribute the TMDS, or other hydrogen donor, as needed. The reaction is determined to be complete when TMDS is no longer detectably being condensed out of the condenser. Following a determination that the reaction is completed, any residual TMDS or other hydrogen donor and any polysiloxanes in the liquid phase are then removed through, by non-limiting example, vacuum distillation, physical separation, or phase separation. The vacuum distillation may be performed at an elevated temperature, such as between about 100 C to about 250 C depending on the degree of polymerization of the polysiloxanes. The degree of polymerization may be determined by the amount of residual TMDS, the amount of catalyst used, and the reaction time. Following separation of the remaining unreacted hydrogen donor, the catalyst may be deactivated by various refining processes such as, by non-limiting example, a brine wash, treatment with an absorbent material such as activated carbon, silica, bleaching earth, or other process capable of deactivating and/or removing the catalyst material. In various implementations, catalyst deactivation may be performed before or after removal of the residual TMDS and/or the polysiloxanes.

The reaction, including conversion, ether/ester distribution, and identification for the wax-ether product, may be monitored through observing the saponification (SAP) value measured using the official method of the American Oil Chemists' Society file name Cd 3-25 (AOCS Cd 3-25). The saponification value is the amount of alkali necessary to saponify a definite quantity of the test sample. It is expressed as the number of milligrams of potassium hydroxide (KOH) required to saponify 1 gram of the test sample. In the examples of reactions disclosed herein, the reaction was also monitored with an Agilent 6890 Gas Chromatograph (GC) with a 5973N Mass Spectrometer using electron ionization (EI) equipped with a cool-on column inlet. The source temperature was maintained at 250 C and the quadrupole temperature was maintained at 150 C. The column used was a Restek RTX-65TG, 30 m, 250 µm diameter, and 0.1 µm film thickness. Temperature programming on the GC was initiated at 60 C for 1 minute and increased to 350 C at 4 C/min, holding at 350 C for 5 min. Gas flowrate was maintained at 1 mL/min using research grade helium. The mass spectral database National Institute of Standards and Technology (NIST) 12 (NIST Thermophysical Properties of Pure Fluids Database: Version 3.0) was utilized for identification when available. Various AOCS standard procedures were used to evaluate additional properties of the wax ethers, such as AOCS Cd 8-53 for peroxide value, AOCS Ci 4-91 for acid value, AOCS Cd 1-25 for iodine value, AOCS Cc 18-80 for dropping point, and Cd 12b-92 for oxidative stability index (OSI).

In particular implementations, the reaction may begin using wax esters as the reactants. The wax ester species include esterified fatty acids and fatty alcohols with chain lengths from C14 to C26 with varying degrees of unsaturation that may form complete wax esters ranging from C24 to C52. Also included may be those esterified fatty acids and fatty alcohols used to produce transesterified products like those marketed under the tradenames FLORAESTERS® 15, FLORAESTERS® 20, FLORAESTERS® 30, FLORAESTERS® 60, or FLORAESTERS® 70 by International Flora Technologies, LTD. of Chandler, Ariz. Examples of such corresponding fatty alcohols and fatty esters that may be used in various implementations corresponding with the aforementioned tradenamed products are included in Table 1 (below).

TABLE 1

| Wax Ester | Alcohol | Acid |
|---|---|---|
| C36 | Hexadecanyl | Eicosanoate |
| | Hexadecanyl | (11Z)-Eicos-11-enoate |
| | (9Z)-Hexadec-9-enyl | Eicosanoate |
| | (9Z)-Hexadec-9-enyl | (11Z)-Eicos-11-enoate |
| | Octadecanyl | Octadecanoate |
| | Octadecanyl | (9Z)-Octadec-9-enoate |
| | (9Z)-Octadec-9-enyl | (9Z)-Octadec-9-enoate |
| | Eicosanyl | Hexadecanoate |
| | Eicosanyl | (9Z)-Hexadec-9-enoate |
| | (11Z)-Eicos-11-enyl | Hexadecanoate |
| | (11Z)-Eicos-11-enyl | (9Z)-Hexadec-9-enoate |
| C38 | Hexadecanyl | Docosanoate |
| | Hexadecanyl | (13Z)-Docos-13-enoate |
| | (9Z)-Hexadec-9-enyl | Docosanoate |
| | (9Z)-Hexadec-9-enyl | (13Z)-Docos-13-enoate |
| | Octadecanyl | Eicosanoate |
| | Octadecanyl | (11Z)-Eicos-11-enoate |
| | (9Z)-Octadec-9-enyl | Eicosanoate |
| | (9Z)-Octadec-9-enyl | (11Z)-Eicos-11-enoate |
| | Eicosanyl | Octadecanoate |
| | Eicosanyl | (9Z)-Octadec-9-enoate |
| | (11Z)-Eicos-11-enyl | Octadecanoate |
| | (11Z)-Eicos-11-enyl | (9Z)-Octadec-9-enoate |
| | Docosanyl | Hexadecanoate |
| | Docosanyl | (9Z)-Hexadec-9-enoate |
| | (13Z)-Docos-13-enyl | Hexadecanoate |
| | (13Z)-Docos-13-enyl | (9Z)-Hexadec-9-enoate |
| C40 | Hexadecanyl | Tetracosanoate |
| | Hexadecanyl | (15Z)-Tetracos-15-enoate |
| | (9Z)-Hexadec-9-enyl | Tetracosanoate |
| | (9Z)-Hexadec-9-enyl | (15Z)-Tetracos-15-enoate |
| | Octadecanyl | Docosanoate |
| | Octadecanyl | (13Z)-Docos-13-enoate |
| | (9Z)-Octadec-9-enyl | Docosanoate |
| | (9Z)-Octadec-9-enyl | (13Z)-Docos-13-enoate |
| | Eicosanyl | Eicosanoate |
| | Eicosanyl | (11Z)-Eicos-11-enoate |
| | (11Z)-Eicos-11-enyl | (11Z)-Eicos-11-enoate |
| | Docosanyl | Octadecanoate |
| | Docosanyl | (9Z)-Octadec-9-enoate |
| | (13Z)-Docos-13-enyl | Octadecanoate |
| | (13Z)-Docos-13-enyl | (9Z)-Octadec-9-enoate |
| | Tetracosanyl | Hexadecanoate |
| | Tetracosanyl | (9Z)-Hexadec-9-enoate |
| | (15Z)-Tetracos-15-enyl | Hexadecanoate |
| | (15Z)-Tetracos-15-enyl | (9Z)-Hexadec-9-enoate |
| C42 | Octadecanyl | Tetracosanoate |
| | Octadecanyl | (15Z)-Tetracos-15-enoate |
| | (9Z)-Octadec-9-enyl | Tetracosanoate |
| | (9Z)-Octadec-9-enyl | (15Z)-Tetracos-15-enoate |
| | Eicosanyl | Docosanoate |
| | Eicosanyl | (13Z)-Docos-13-enoate |
| | (11Z)-Eicos-11-enyl | Docosanoate |
| | (11Z)-Eicos-11-enyl | (13Z)-Docos-13-enoate |

TABLE 1-continued

| Wax Ester | Alcohol | Acid |
|---|---|---|
| | Docosanyl | Docosanoate |
| | Docosanyl | (13Z)-Docos-13-enoate |
| | (13Z)-Docos-13-enyl | (13Z)-Docos-13-enoate |
| | Tetracosanyl | Octadecanoate |
| | Tetracosanyl | (9Z)-Octadec-9-enoate |
| | (15Z)-Tetracos-15-enyl | Octadecanoate |
| | (15Z)-Tetracos-15-enyl | (9Z)-Octadec-9-enoate |
| C44 | Eicosanyl | Tetracosanoate |
| | Eicosanyl | (15Z)-Tetracos-15-enoate |
| | (11Z)-Eicos-11-enyl | Tetracosanoate |
| | (11Z)-Eicos-11-enyl | (15Z)-Tetracos-15-enoate |
| | Docosanyl | Docosanoate |
| | Docosanyl | (13Z)-Docos-13-enoate |
| | (13Z)-Docos-13-enyl | (13Z)-Docos-13-enoate |
| | Tetracosanyl | Eicosanoate |
| | Tetracosanyl | (11Z)-Eicos-11-enoate |
| | (15Z)-Tetracos-15-enyl | Eicosanoate |
| | (15Z)-Tetracos-15-enyl | (11Z)-Eicos-11-enoate |
| C46 | Docosanyl | Tetracosanoate |
| | Docosanyl | (15Z)-Tetracos-15-enoate |
| | (13Z)-Docos-13-enyl | Tetracosanoate |
| | (13Z)-Docos-13-enyl | (15Z)-Tetracos-15-enoate |
| | Tetracosanyl | Docosanoate |
| | Tetracosanyl | (13Z)-Docos-13-enoate |
| | (15Z)-Tetracos-15-enyl | Docosanoate |
| | (15Z)-Tetracos-15-enyl | (13Z)-Docos-13-enoate |

These various reactants may be, in various implementations, products of the transesterification of jojoba oil and hydrogenated jojoba oil having varying iodine values. A reaction was done with each of these wax ester reactants as described above, including the same catalyst and hydrogen donor previously described. The resulting product of the etherification reaction using these reactants, an ether lipid, demonstrates distinctive properties that were not present in the starting reactants. These properties are summarized in Table 2 (below) for each of the respective wax ester products versus the corresponding wax ether product. While many of the physical properties of the wax ether product are similar to the wax ester product, those for SAP value and oxidative stability index (OSI) differ markedly. These characteristics may show parity with shorter chain length ethers that are not jojoba derived, such as mixtures containing C14-C26 fatty acids and fatty alcohols of varying saturation. However, the difference in OSI value shows that the wax ether product is more stable than the corresponding wax ether product.

TABLE 2

| Test | Ether 20 | Floraesters 20 | Ether 30 | Floraesters 30 | Ether 60 | Floraesters 60 | Ether 70 | Floraesters 70 |
|---|---|---|---|---|---|---|---|---|
| PEROXIDE VALUE | 0 | 0 | 0 | 0 | 0 | 0 | 0 | 0 |
| ACID VALUE | 0.73 | 0.69 | 0.71 | 0.72 | 0.69 | 0.7 | 0.68 | 0.67 |
| IODINE VALUE | 61.72 | 65.33 | 55.28 | 57.66 | 42.87 | 43.29 | 0 | 0 |
| SAP VALUE | 1.2 | 91.3 | 0.9 | 92.4 | 0.7 | 93.1 | 1.2 | 93.7 |
| DROPPING POINT (° C.) | 46.9 | 46 | 51.2 | 50.3 | 55.6 | 54.1 | 69.3 | 68.9 |
| OSI (hrs) | 138 | 115 | 139 | 122 | 151 | 136 | 220 | 180 |

In another implementation of a method of forming wax esters from triglyceride input material, the transesterification product of moringa oil and hydrogenated moringa oil was used as the reactant under the same conditions described above, including using the same catalyst and hydrogen donor. Conversion was monitored by quantitating the triglyceride component using SAP value and normal phase high pressure liquid chromatography (HPLC) using an Agilent 1160 HPLC with a quaternary pump and an Alltech 2000 ELSD detector using 1.8 L/min nitrogen at 50 C. Separation was done with an Agilent RX-SIL 4.6×50 mm, 1.8 μm particle size column maintained at 45 C. The mobile phase consisted of 100% hexane to 60% hexane/40% ethyl acetate over 15 minutes at 1 mL/min.

The difference in the various input materials in the examples provided in this document did not have any observed effect on reaction time as both wax esters and triglycerides of varying degrees of saturation were observed to be fully converted within 30 minutes.

The most notable difference between the wax-ester and triglyceride etherification products was that the triglycerol ether showed a remarkable change in melting point compared to the starting material despite maintaining a similar iodine value. The transesterification product of moringa oil and hydrogenated moringa with an iodine value of 52 had a melting point of 45 C, making it a solid at room temperature. Unexpectedly, in contrast, the triglycerol ether equivalent of the moringa oil had a primary solid to liquid transition at 16 C, and resembled a milky liquid at room temperature with the secondary transition from white to transparent occurring at 42 C. This optical behavior of the liquid likely indicates an "unstable" polymorphic property that is not observed in the wax-ethers variants.

It is also notable that the iodine value as found in AOCS Cd 1-25 slightly decreases during the ether process indicating a decrease in the concentration of double bonds present on the fatty acid or fatty alcohol chains. Without being bound by any theory, this appears to be due to an oxidation reaction that effectively cleaves the chain at the double bond, forming a short chain ether and alcohol. The oxidation of the double bond containing wax-esters is apparent in the minor changes in carbon chain length distributions between the reactants and products shown in the graph of FIG. 1. The fatty acids and fatty alcohols in jojoba and moringa oils have double bonds in the omega-9 position. The oxidative cleavage at the omega-9 position yields the alcohol 1-nonanol, an alcohol with 9 carbons and a distinct human.

Figure 2:
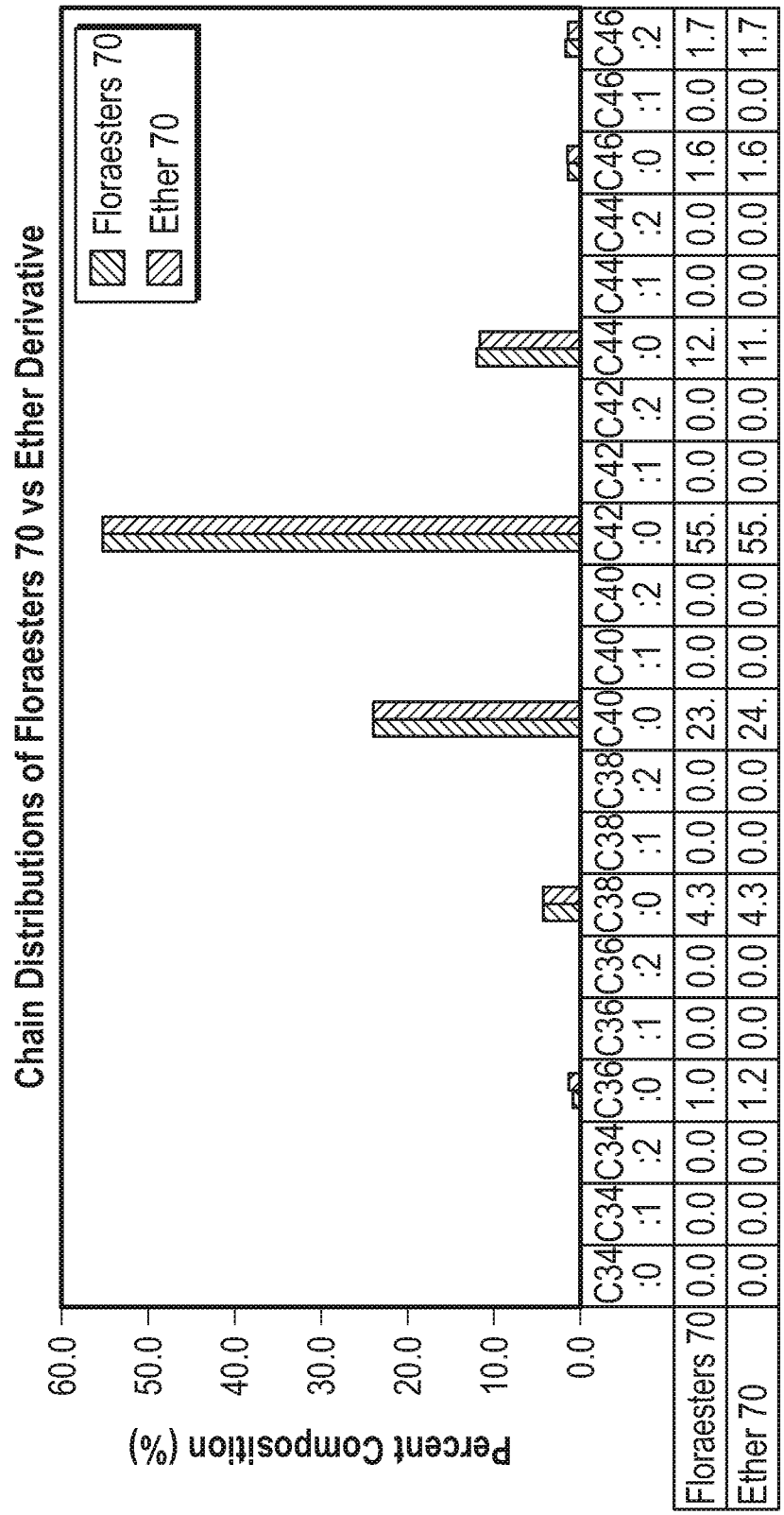
FIG. 2 is a graph illustrating carbon chain length distributions between a wax ester product marketed under the tradename FLORAESTERS® 70 as a reactant and the resulting ether derivative in an implementation of a method of forming wax ethers.
Figure 3:
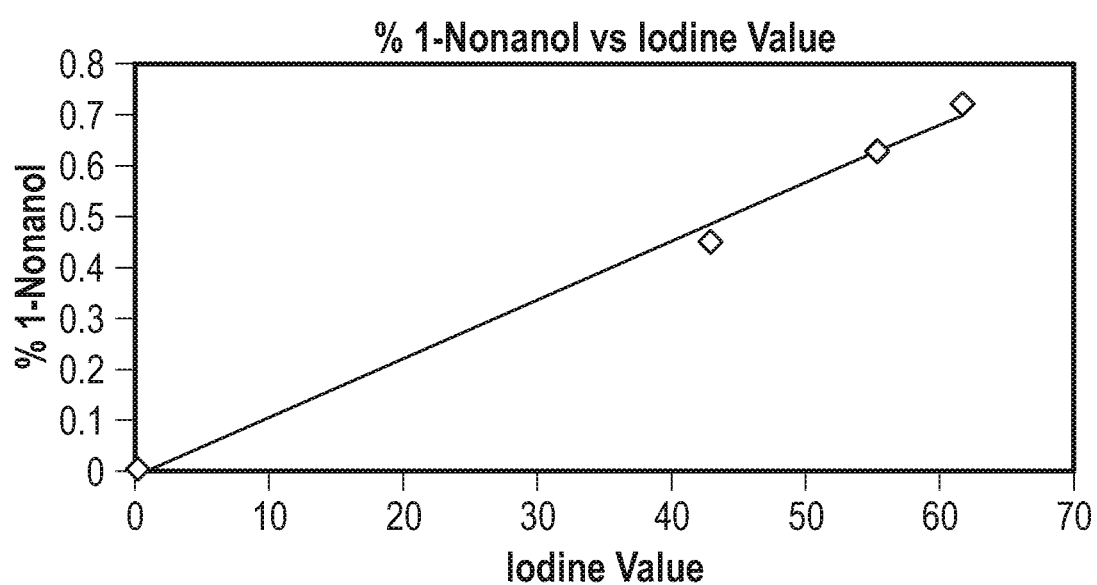
FIG. 3 is a graph comparing the percentage of 1-nonanol and iodine values of products of an implementation of a method of forming wax ethers.

The reaction also does not show a notable difference between the carbon chain length distribution between the ether product or the ester product when using input materials like those used to produce FLORAESTERS® 70 which do not have double bonds as shown in the graph of FIG. 2. Quantitative and qualitative analysis of 1-nonanol was done using the GC-MS method mentioned above. The concentration of synthesized 1-nonanol decreases proportionally across the products as the concentration of double bonds and iodine value decreases as seen in the graph in FIG. 3. This behavior is unexpected, as previous work indicates this observed side reaction to form 1-nonanol does not occur and assumes the conversion is limited to the reductive reaction of carboxylic acids or esters to alcohols or ethers as described in PCT Application Publication No. WO2013010747 to Metzger et al, entitled "Process For Reducing Carboxylic Esters Or Carboxylic Lactones To The Corresponding Ethers," filed Jun. 22, 2012, the entirety of which is hereby incorporated by reference. Under previously mentioned reaction conditions, the reducing agent is observed to simultaneously oxidize alkenes to alcohols (1-nonanol) to a certain degree while still reducing esters to ethers.

The foregoing indicates that for wax esters, the etherification reaction disclosed herein appears to be nonspecific and works to cleaves double bonds not limited to fatty acids or fatty alcohols. Thus, it has been observed that inherent color bodies, such as carotenoids and tocopherols in the reactants, also undergo this oxidation process readily during the reaction. The oxidation of the double bonds on these molecules removes the optical activity of the molecules and renders the final product devoid of color (optically clear). Referring to Table 3 (below), the observed data contrasting the optical characteristics of the ester and ether products, and including a sample which was spiked with the addition of 500 ppm alpha-tocopherol in the input material is illustrated. As indicated, the ether product, whether spiked or not, was substantially optically clear following the process, as both the tocopherols and beta carotene present in the reactants were not detectable (noted as ND) after the reaction. This result was also unexpected in view of the teachings of previous work. The color and amount of color bodies of the final product was measured using the Lovibond method as found in AOCS file Cc 13e-92 and an Agilent 1160 HPLC with a quaternary pump and an Alltech 2000 Evaporative light scattering detector (ELSD) using 1.8 L/min nitrogen at 40° C. Separation was done with an Agilent RX-SIL 4.6×50 mm, 1.8 μm particle size column maintained at 45° C. The mobile phase included 98% hexane to 2% isopropanol isocratically flowed for 15 minutes at 1 L/min. The diode array detector (DAD) was set to monitor beta carotene at 475 nm and alpha tocopherol at 291 nm.

TABLE 3

|  | Lovi Color | Tocopherol (ppm) | Beta Carotene (ppm) |
| --- | --- | --- | --- |
| Floraesters 20 | 4.2Y, 0.9R | 127 | 43 |
| Ethers 20 | 0.3Y, 0.2R | ND | ND |
| Floraesters 20 Spiked | 4.8Y, 1.1R | 721 | 76 |
| Ether 20 Spiked | 0.3Y, 0.3R | ND | ND |

An additional unexpected result, which was not disclosed or taught in any previous work, relates to the effect of the deactivation of these color bodies which serve as natural antioxidants. It was observed that the deactivation of the color bodies did not result in any reduction in the oxidative stability—something clearly unexpected and novel. One would assume that the lack of antioxidants would decrease the Oxidative Stability Index using the method of AOCS file Cd 12b-92. However, the additional surprisingly unexpected result of a significant increase in OSI values was observed as previously illustrated in Table 1 (above). Given that the natural antioxidants in the reactant material were already oxidized in the reaction and could not contributed to the OSI value at this point, the result that the ether product exhibited much higher OSI was not predicted or a predictable result in view of what is taught and disclosed in previous work.

In various implementations, the distribution chain lengths (C36, C38, C40, C42, C44, and C46) did not substantially change during the conversion from a wax-ester to a wax-ether. In some implementations, the ether products have a notable observed increase in spreading properties on the skin. An additional subjective property noted with the ether products is a "less greasy" feel when compared to the FLORAESTERS starting materials. An additional subjective property noted with implementations of the ether products is a unique "film forming" property that is absent in the ester products that is described as a "non-volatile silicone" or "siliconeized" feel.

The feel test results for the ether products were substantiated in a consumer test panel. The ether derivatives were compared to dimethicone CS100, a commonly used silicone in cosmetic applications. The materials were compared in a neat application. It was found that ethers resembled dimethicone in spread, absorbency, and feel immediately and post 30 minutes after application. The ethers also displayed similar gloss, stickiness, slipperiness, amount of residue, silkiness/smoothness, greasiness, and moisturization of the skin when compared to dimethicone CS100. The ability of the ether product to mimic a silicone's subjective properties was unexpected, given the ether product does not contain silicon in its chemical structure.

In places where the description above refers to particular implementations of wax ethers and implementing components, sub-components, methods and sub-methods, it should be readily apparent that a number of modifications may be made without departing from the spirit thereof and that these implementations, implementing components, sub-components, methods and sub-methods may be applied to other wax ethers.

What is claimed is:

1. A method of forming an ether composition, the method comprising:
providing a batch of lipids;
drying the batch of lipids;
cooling the batch of lipids;
dosing with a catalyst, the batch of lipids at 0.1% to 0.3% by weight of the batch of lipids;
dissolving the catalyst to form a homogenous solution;
adding at least a molar equivalent of a hydrogen donor to the homogenous solution; and
sealing and maintaining the homogenous solution and the hydrogen donor under atmospheric pressure under reflux until a chemical reaction between the homogenous solution and the hydrogen donor forms a product comprising an ether.

2. The method of claim 1, wherein drying the batch of lipids comprises heating the batch of lipids at 100 C under agitation and vacuum.

3. The method of claim 1, wherein cooling the batch of lipids comprises cooling the batch of lipids to 5 C-10 C above the melting point of the batch of lipids under agitation and vacuum.

4. The method of claim 1, further comprising removing a residue of the hydrogen donor through one of vacuum distillation or physical separation.

5. The method of claim 1, further comprising capturing and redistributing the hydrogen donor using a condenser during the chemical reaction.

6. The method of claim 1, wherein the batch of lipids comprises one of wax esters or triglycerides.

7. The method of claim 1, wherein the hydrogen donor comprises 1,1,3,3-tetramethyldisiloxane (TMDS).

8. The method of claim 1, wherein the catalyst is a metal halide.

9. A method of forming an ether composition, the method comprising:
providing a batch of triglycerides;
drying the batch of triglycerides;
cooling the batch of triglycerides;
dosing with a catalyst, the batch of triglycerides at 0.1% to 0.3% by weight of the batch of triglycerides;
dissolving the catalyst to form homogenous solution;
adding at least a molar equivalent of a hydrogen donor to the homogenous solution; and
sealing and maintaining the homogenous solution and the hydrogen donor under atmospheric pressure under reflux until a chemical reaction between the homogenous solution and the hydrogen donor forms a product comprising an ether.

10. The method of claim 9, wherein drying the batch of triglycerides comprises heating the batch of triglycerides at 100 C under agitation and vacuum.

11. The method of claim 9, wherein cooling the batch of triglycerides comprises cooling the batch of triglycerides to 5 C-10 C above the melting point of the batch of triglycerides under agitation and vacuum.

12. The method of claim 9, further comprising removing a residue of the hydrogen donor through one of vacuum distillation or physical separation.

13. The method of claim 9, further comprising capturing and redistributing the hydrogen donor using a condenser during the chemical reaction.

14. The method of claim 9, wherein a product of the chemical reaction comprises an iodine value of 52 and a melting point of 45 C.

15. A method of forming a wax ether composition, the method comprising:
providing a batch of wax esters;
drying the batch of wax esters;
cooling the batch of wax esters;
dosing with a catalyst, the batch of triglycerides at 0.1% to 0.3% by weight of the batch of wax esters; and
dissolving catalyst to form homogenous solution;
adding at least a molar equivalent of hydrogen donor to the homogenous solution; and
sealing and maintaining the homogenous solution and the hydrogen donor under atmospheric pressure under reflux until a chemical reaction between the homogenous solution and the hydrogen donor forms a product comprising an ether.

16. The method of claim 15, wherein the batch of wax esters comprises wax esters comprising carbon chain lengths ranging from C24 to C52.

17. The method of claim 15, wherein drying the batch of wax esters comprises heating the batch of wax esters at 100 C under agitation and vacuum.

18. The method of claim 15, wherein cooling the batch of wax esters comprises cooling the batch of wax esters to 5-10° C. above the melting point of the batch of wax esters under agitation and vacuum.

19. The method of claim 15, further comprising removing a residue of the hydrogen donor through one of vacuum distillation or physical separation.

20. The method of claim 15, further comprising capturing and redistributing the hydrogen donor using a condenser during the chemical reaction.

* * * * *